(12) United States Patent
Kani et al.

(10) Patent No.: US 8,440,763 B2
(45) Date of Patent: May 14, 2013

(54) COSMETIC COMPOSITION COMPRISING SILICONE PARTICLES

(75) Inventors: Toshiyuki Kani, Tokyo (JP); Christophe Dumousseaux, Tokyo (JP)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/449,799

(22) Filed: Jun. 9, 2006

(65) Prior Publication Data

US 2006/0293431 A1    Dec. 28, 2006

Related U.S. Application Data (60) Provisional application No. 60/690,500, filed on Jun. 15, 2005.

(30) Foreign Application Priority Data

Jun. 9, 2005   (FR) ...................................... 05 51553

(51) Int. Cl.
 *C08L 83/04* (2006.01)
(52) U.S. Cl.
 USPC ........................... 524/588; 424/59; 424/70.12
(58) Field of Classification Search .................. 524/588; 424/59, 70.12
 See application file for complete search history.

(56) References Cited

U.S. PATENT DOCUMENTS

| | | | |
|---|---|---|---|
| 5,236,986 A | 8/1993 | Sakuta | |
| 5,412,004 A | 5/1995 | Tachibana et al. | |
| 5,496,543 A | 3/1996 | Lagrange et al. | |
| 5,583,234 A | 12/1996 | Lagrange et al. | |
| 5,695,747 A | 12/1997 | Forestier et al. | |
| 5,776,497 A | 7/1998 | Lagrange et al. | |
| 5,811,487 A | 9/1998 | Schulz, Jr. et al. | |
| 5,837,793 A | 11/1998 | Harashima et al. | |
| 6,258,345 B1 | 7/2001 | Rouquet et al. | |
| 2002/0018790 A1* | 2/2002 | Vatter et al. | 424/401 |
| 2003/0108498 A1* | 6/2003 | Stephens et al. | 424/63 |
| 2005/0118218 A1 | 6/2005 | Cassin | |
| 2005/0220740 A1* | 10/2005 | Dumousseaux | 424/64 |
| 2005/0220741 A1* | 10/2005 | Dumousseaux | 424/64 |
| 2006/0034875 A1 | 2/2006 | Nakanishi et al. | |

FOREIGN PATENT DOCUMENTS

| | | |
|---|---|---|
| EP | 0 293 795 | 12/1988 |
| EP | 0 295 886 | 12/1988 |
| EP | 0 518 773 | 12/1992 |
| EP | 0 908 175 | 4/1999 |
| EP | 1 530 961 | 5/2005 |
| EP | 1 579 841 | 9/2005 |
| FR | 2 856 921 | 1/2005 |
| FR | 2 867 676 | 9/2005 |
| JP | 2000-191789 | 7/2000 |
| JP | 2003-128788 | 5/2003 |
| JP | 2003-277233 | 10/2003 |
| JP | 2003-313105 | 11/2003 |
| WO | WO 93/13744 | 7/1993 |
| WO | WO 93/13745 | 7/1993 |
| WO | WO 2004/024798 | 3/2004 |

OTHER PUBLICATIONS

Wikipedia (http://en.wikipedia.org/wiki/Emulsion) (date unknown).*
European Search Report for EP 1 731 136, dated Sep. 27, 2006.
Japanese Office Action issued Feb. 7, 2012 in Patent Application No. 2006-159934 (English-language translation only).
English language Derwent abstract for FR 2 856 921, (2005).
English language Derwent abstract for JP 2000-191789, (2000).
English language Derwent abstract for JP 2003-128788, (2003).
*International Cosmetic Ingredient Dictionary and Handbook*, pp. 371-386 and 524-528, The Cosmetic, Toiletry, and Fragrance Association (1997).
French Search Report for FR 05 51553, mailed Mar. 10, 2006 (corresponding to the present application).

* cited by examiner

*Primary Examiner* — Kuo-Liang Peng
(74) *Attorney, Agent, or Firm* — Oblon, Spivak, McClelland, Maier & Neustadt, L.L.P.

(57) ABSTRACT

Disclosed herein is a composition comprising concave particles of a silicone material and a fatty phase comprising at least one oil and at least one non-spherical silicone elastomer. The composition may make it possible to obtain a make-up for the skin and/or lips which is non-drying and/or which does not exhibit tightness and/or which is comfortable.

48 Claims, 1 Drawing Sheet

COSMETIC COMPOSITION COMPRISING SILICONE PARTICLES

This application claims benefit of U.S. Provisional Application No. 60/690,500, filed Jun. 15, 2005, the contents of which are incorporated herein by reference.

This application also claims benefit of priority under 35 U.S.C. §119 to French Patent Application No. FR 05 51553, filed Jun. 9, 2005, the contents of which are also incorporated herein by reference.

Disclosed herein is a cosmetic composition intended to be applied to human keratinous substances, such as the skin, lips, eyelashes, eyebrows, nails, and/or hair, and, in at least one embodiment, the skin and/or lips.

The composition according to the present disclosure may be a make-up and/or care composition.

The composition may be a make-up composition, chosen, for example, from products for making up the lips (lipstick), foundations, eyeshadows, face powders, concealers, eyeliners, products for making up the body, mascaras, nail varnishes, and products for making up the hair.

The composition may be a care composition, chosen, for example, from products for caring for the skin of the body and/or face, such as an anti-sun products and products for coloring the skin (such as self-tanning products). The composition may also be a hair product, for instance, a product for form retention of the hairstyle and/or shaping the hair.

Cosmetic compositions often comprise thickening agents in order to obtain a viscosity suited to the use of a product. In the case of liquid compositions, the thickening agent may make it possible to obtain the desired viscosity of the final composition. In the case of compositions in the form of powders, a thickening agent may be used to obtain the desired properties with respect to the binder. For instance, if the binder is too liquid, the powder obtained may exhibit poor slip on application.

The thickening agent may be introduced, for example, into a fatty phase of the composition, which generally comprises at least one oil.

European Patent Application No. 0 908 715 discloses the use, as thickening agents for oily media, of silicone elastomers which provide various advantageous properties, such as improved texture and softness to the touch.

However, these silicone elastomers have the disadvantage of being expensive. Furthermore, in order to be able to satisfactorily thicken oils, or even to obtain a macroscopic gel, it is often necessary to use a high level of silicone elastomers, i.e., at least 20% by weight of active material of silicone elastomers. In addition, the oily gels obtained with these elastomers may cause the composition to have a greasy or tacky feel.

It is also known to introduce specific oil-absorbing particles, such as porous silicas, into cosmetic compositions in order to increase the viscosity of a liquid fatty phase, as disclosed in French Patent Application No. 2 856 921. However, after these compositions are applied to the skin, the make-up obtained may exhibit a drying effect due to the presence of the porous particles. This may result in a feeling of discomfort for the user, such as tightness of the skin.

There thus exists a need for cosmetic compositions comprising a thickening agent, making it possible to thicken the oily phase of the composition, and not exhibiting a drying effect after application to the skin.

There also exists a need for cosmetic compositions exhibiting good properties of spreading and/or slip over the skin and/or lips.

The present inventors have demonstrated that, by combining, in an oily phase, a non-spherical silicone elastomer and concave silicone particles, it is possible to obtain a high viscosity of the oily phase. Furthermore, such a mixture may make it possible to retain good cosmetic properties, such as absence of drying, absence of tightness, softness, comfort, slip and/or spreading.

Thus disclosed herein is a composition comprising concave particles of a silicone material, such as particles in the form of portions of hollow spheres, and a fatty phase comprising at least one oil and at least one non-spherical silicone elastomer. Also disclosed herein is a composition comprising a fatty phase comprising concave silicone particles, at least one oil, and at least one non-spherical silicone elastomer. The composition may be a cosmetic and/or dermatological composition.

Further disclosed herein is a cosmetic (non-therapeutic) method for making up and/or caring for keratinous substances comprising applying a composition of the present disclosure to the keratinous substances. In at least one embodiment, the keratinous substances may be the skin and/or lips.

In addition, disclosed herein is a method for producing a deposited layer, such as a make-up layer, on the skin and/or lips which is non-drying and/or which does not exhibit tightness and/or which is comfortable comprising applying a composition of the present disclosure to the skin and/or lips.

Silicone Elastomers

The composition according to the present disclosure comprises at least one non-spherical silicone elastomer. The at least one silicone elastomer may or may not be emulsifying.

In at least one embodiment, the composition according to the present disclosure may comprise at least one non-emulsifying silicone elastomer.

As used herein, the term "non-emulsifying silicone elastomer" denotes organopolysiloxane elastomers not comprising a hydrophilic chain, such as polyoxyalkylene and polyglycerol units.

The non-emulsifying silicone elastomer may be a crosslinked organopolysiloxane elastomer which may be obtained by a crosslinking addition reaction of a diorganopolysiloxane comprising at least one silicon-bonded hydrogen and of a diorganopolysiloxane having silicon-bonded groups comprising ethylenic unsaturation, optionally in the presence of a platinum catalyst; or by a crosslinking condensation/dehydrogenation reaction between a diorganopolysiloxane comprising hydroxyl endings and a diorganopolysiloxane comprising at least one silicon-bonded hydrogen, optionally in the presence of an organotin compound; or by a crosslinking condensation reaction of a diorganopolysiloxane comprising hydroxyl endings and of a hydrolysable organopolysilane; or by thermocrosslinking of an organopolysiloxane, optionally in the presence of an organoperoxide catalyst; or by crosslinking of an organopolysiloxane by high energy radiation, such as gamma rays, ultraviolet rays, and an electron beam.

In at least one embodiment, the crosslinked organopolysiloxane elastomer may be obtained by a crosslinking addition reaction (A2) of a diorganopolysiloxane comprising at least two hydrogens each bonded to a silicon and (B2) of a diorganopolysiloxane having at least two silicon-bonded groups comprising ethylenic unsaturation, optionally in the presence (C2) of a platinum catalyst, as disclosed, for example, in European Patent Application No. 0 295 886.

In another embodiment, the organopolysiloxane may be obtained by reaction of a dimethylpolysiloxane comprising dimethylvinylsiloxy endings and of a methylhydropolysiloxane comprising trimethylsiloxy endings, in the presence of a platinum catalyst.

In a further embodiment, the compound (A2) is the base reactant for the formation of an organopolysiloxane elastomer and the crosslinking is carried out by an addition reaction of the compound (A2) with the compound (B2) in the presence of the catalyst (C2).

The compound (A2) may be a diorganopolysiloxane having at least two lower (for example, $C_2$-$C_4$) alkenyl groups; wherein the lower alkenyl group may be chosen from vinyl, allyl, and propenyl groups. These lower alkenyl groups may be situated in any position on the organopolysiloxane molecule, for example, at the ends of the organopolysiloxane molecule. The organopolysiloxane (A2) may have a structure chosen from branched-chain, linear-chain, cyclic, and network structures, and in at least one embodiment, a linear-chain structure. The compound (A2) may have a viscosity ranging from the liquid state to the gum state, for example, a viscosity of at least 100 centistokes at 25° C.

The organopolysiloxanes (A2) may be chosen from methylvinylpolysiloxanes, methylvinylsiloxane/dimethylsiloxane copolymers, dimethylpolysiloxanes comprising dimethylvinylsiloxy endings, dimethylsiloxane/methylphenylsiloxane copolymers comprising dimethylvinylsiloxy endings, dimethylsiloxane/diphenylsiloxane/methylvinylsiloxane copolymers comprising dimethylvinylsiloxy endings, dimethylsiloxane/methylvinylsiloxane copolymers comprising trimethylsiloxy endings, dimethylsiloxane/methylphenylsiloxane/methylvinylsiloxane copolymers comprising trimethylsiloxy endings, methyl(3,3,3-trifluoropropyl)polysiloxanes comprising dimethylvinylsiloxy endings, and dimethylsiloxane/methyl(3,3,3-trifluoropropyl)siloxane copolymers comprising dimethylvinylsiloxy endings.

The compound (B2) may be an organopolysiloxane having at least two silicon-bonded hydrogens in each molecule and thus may be the crosslinking agent of the compound (A2).

In at least one embodiment of the present disclosure, the sum of the number of ethylenic groups per molecule of the compound (A2) and the number of silicon-bonded hydrogen atoms per molecule of the compound (B2) is at least 4.

The compound (B2) can have any molecular structure, such as linear-chain, branched-chain, and cyclic structures.

The compound (B2) may have a viscosity at 25° C. ranging from 1 to 50 000 centistokes, for example, a viscosity such that compound (B2) is highly miscible with the compound (A).

It at least one embodiment the compound (B2) may be added in an amount such that the molecular ratio of the total amount of silicon-bonded hydrogen atoms in the compound (B2) to the total amount of all the groups comprising ethylenic unsaturation in the compound (A2) ranges from 1/1 to 20/1.

The compound (B2) may be chosen from methylhydropolysiloxanes comprising trimethylsiloxy endings, dimethylsiloxane/methylhydrosiloxane copolymers comprising trimethylsiloxy endings, and dimethylsiloxane/methylhydrosiloxane cyclic copolymers.

The compound (C2) is the catalyst of the crosslinking reaction and may be chosen, for example, from chloroplatinic acid, chloroplatinic acid/olefin complexes, chloroplatinic acid/alkenylsiloxane complexes, chloroplatinic acid/diketone complexes, platinum black, and platinum-on-support.

The catalyst (C2) may be present in an amount ranging from 0.1 to 1000 parts by weight, for example, from 1 to 100 parts by weight, as platinum metal proper per 1000 parts by weight of the total amount of the compounds (A2) and (B2).

Other organic groups may be silicon-bonded in the organopolysiloxanes (A2) and (B2) described above, for example, alkyl groups, such as methyl, ethyl, propyl, butyl, and octyl groups; substituted alkyl groups, such as 2-phenylethyl, 2-phenylpropyl, and 3,3,3-trifluoropropyl groups; aryl groups, such as phenyl, tolyl, and xylyl groups; substituted aryl groups, such as phenylethyl; and substituted monovalent hydrocarbon groups, such as epoxy, carboxylate ester, and mercapto groups.

The non-emulsifying silicone elastomer may be mixed with at least one hydrocarbon oil and/or one silicone oil to form a gel. In these gels, the non-emulsifying elastomer may be in the form of non-spherical particles.

Examples of non-emulsifying elastomers include, but are not limited to, those sold under the names "KSG-6", "KSG-15", "KSG-16", "KSG-18", "KSG-31", "KSG-32", "KSG-33", "KSG-41", "KSG-42", "KSG-43", and "KSG44" by Shin Etsu, "DC 9040", "DC 9041", "DC 9509", "DC 9505", and "DC 9506" by Dow Corning, "Gransil" by Grant Industries, and "SFE 839" by General Electric.

As used herein, the term "emulsifying silicone elastomer" is understood to mean a silicone elastomer comprising at least one hydrophilic chain.

The emulsifying silicone elastomer may be chosen from polyoxyalkylenated silicone elastomers.

The polyoxyalkylenated silicone elastomer may be a crosslinked organopolysiloxane which may be obtained by a crosslinking addition reaction of a diorganopolysiloxane comprising at least one silicon-bonded hydrogen and of a polyoxyalkylene having at least two groups comprising ethylenic unsaturation.

In at least one embodiment, the crosslinked polyoxyalkylenated organopolysiloxane may be obtained by a crosslinking addition reaction (A1) of a diorganopolysiloxane comprising at least two hydrogens each bonded to a silicon and (B1) of a polyoxyalkylene having at least two groups comprising ethylenic unsaturation, optionally in the presence (C1) of a platinum catalyst, as disclosed, for example, in U.S. Pat. Nos. 5,236,986 and 5,412,004.

In another embodiment, the organopolysiloxane may be obtained by reaction of a polyoxyalkylene (such as polyoxyethylene and/or polyoxypropylene) comprising dimethylvinylsiloxy endings and of a methylhydropolysiloxane comprising trimethylsiloxy endings, in the presence of a platinum catalyst.

The organic groups bonded to the silicon atoms of the compound (A1) may be alkyl groups comprising from 1 to 18 carbon atoms, such as methyl, ethyl, propyl, butyl, octyl, decyl, dodecyl (or lauryl), myristyl, cetyl, and stearyl groups; substituted alkyl groups, such as 2-phenylethyl, 2-phenylpropyl, and 3,3,3-trifluoropropyl groups; aryl groups, such as phenyl, tolyl, and xylyl groups; substituted aryl groups, such as phenylethyl; and substituted monovalent hydrocarbon groups, such as epoxy, carboxylate ester, and mercapto groups.

The compound (A1) may thus be chosen from methylhydropolysiloxanes comprising trimethylsiloxy endings, dimethylsiloxane/methylhydrosiloxane copolymers comprising trimethylsiloxy endings, dimethylsiloxane/methylhydrosiloxane cyclic copolymers, and dimethylsiloxane/methylhydrosiloxane/laurylmethylsiloxane copolymers comprising trimethylsiloxy endings.

The compound (C1) is the catalyst of the crosslinking reaction and may be chosen from chloroplatinic acid, chloroplatinic acid/olefin complexes, chloroplatinic acid/alkenylsiloxane complexes, chloroplatinic acid/diketone complexes, platinum black, and platinum-on-support.

In at least one embodiment, the polyoxyalkylenated silicone elastomers may be formed from divinyl compounds, such as polyoxyalkylenes having at least two vinyl groups, reacting with Si—H bonds of a polysiloxane.

The polyoxyalkylenated silicone elastomer according to the present disclosure may be conveyed in the form of a gel in at least one oil chosen from hydrocarbon and silicone oils. In these gels, the polyoxyalkylenated elastomer may be in the form of non-spherical particles.

Polyoxyalkylenated elastomers are disclosed, for example, in U.S. Pat. Nos. 5,236,986, 5,412,004, 5,837,793, and 5,811,487, the contents of which are incorporated by herein by reference.

Non-limiting examples of suitable polyoxyalkylenated silicone elastomers include those sold under the names "KSG-21", "KSG-20", "KSG-30", "KSG-31", "KSG-32", "KSG-33", "KSG-210", "KSG-310", "KSG-320", "KSG-330", "KSG-340", and "X-226146" by Shin Etsu and "DC 9010" and "DC 9011" by Dow Corning.

The emulsifying silicone elastomer may also be chosen from polyglycerolated silicone elastomers.

The polyglycerolated silicone elastomer may be a crosslinked organopolysiloxane elastomer which may be obtained by the crosslinking addition reaction of a diorganopolysiloxane comprising at least one silicon-bonded hydrogen and of polyglycerolated compounds having groups comprising ethylenic unsaturation, optionally in the presence of a platinum catalyst.

In at least one embodiment, the crosslinked organopolysiloxane elastomer may be obtained by a crosslinking addition reaction (A) of a diorganopolysiloxane comprising at least two hydrogens each bonded to a silicon and (B) of glycerolated compounds having at least two groups comprising ethylenic unsaturation, optionally in the presence (C) of a platinum catalyst.

In another embodiment, the organopolysiloxane may be obtained by reaction of a polyglycerolated compound comprising dimethylvinylsiloxy endings and of a methylhydropolysiloxane comprising trimethylsiloxy endings, in the presence of a platinum catalyst.

In a further embodiment, the compound (A) is the base reactant for the formation of an organopolysiloxane elastomer and the crosslinking is carried out by an addition reaction of the compound (A) with the compound (B) in the presence of the catalyst (C).

The compound (A) may be chosen, for example, from organopolysiloxanes having at least two hydrogen atoms bonded to separate silicon atoms in each molecule.

The compound (A) may exhibit any molecular structure, for example, linear-chain, branched-chain, and cyclic structures.

The compound (A) may have a viscosity at 25° C. ranging from 1 to 50 000 centistokes, for example, a viscosity such that compound (A) is highly miscible with the compound (B).

The organic groups bonded to the silicon atoms of the compound (A) may be chosen from alkyl groups comprising from 1 to 18 carbon atoms, such as methyl, ethyl, propyl, butyl, octyl, decyl, dodecyl (or lauryl), myristyl, cetyl, and stearyl groups; substituted alkyl groups, such as 2-phenylethyl, 2-phenylpropyl, and 3,3,3-trifluoropropyl groups; aryl groups, such as phenyl, tolyl, and xylyl groups; substituted aryl groups, such as phenylethyl groups; and substituted monovalent hydrocarbon groups, such as epoxy, carboxylate ester, and mercapto groups. In at least one embodiment, the organic group may be chosen from methyl, phenyl, and lauryl groups.

The compound (A) may thus be chosen from methylhydropolysiloxanes comprising trimethylsiloxy endings, dimethylsiloxane/methylhydrosiloxane copolymers comprising trimethylsiloxy endings, dimethylsiloxane/methylhydrosiloxane cyclic copolymers, and dimethylsiloxane/methylhydrosiloxane/laurylmethylsiloxane copolymers comprising trimethylsiloxy endings.

The compound (B) may be chosen from polyglycerolated compounds of formula (B'):

(B')

wherein:
m is an integer ranging from 2 to 6,
n is an integer ranging from 2 to 200, for example, from 2 to 100, from 2 to 50, from 2 to 20, from 2 to 10, or from 2 to 5, and in at least one embodiment, equal to 3; and
Gly is chosen from:

In one embodiment, the sum of the number of ethylenic groups per molecule of the compound (B) and of the number of hydrogen atoms bonded to silicon atoms per molecule of the compound (A) is at least 4.

In another embodiment, the compound (A) may be added in an amount such that the molecule ratio of the total amount of hydrogen atoms bonded to silicon atoms in the compound (A) to the total amount of all the groups comprising ethylenic unsaturation in the compound (B) ranges from 1/1 to 20/1.

The compound (C) is the catalyst of the crosslinking reaction and may be chosen from chloroplatinic acid, chloroplatinic acid/olefin complexes, chloroplatinic acid/alkenylsiloxane complexes, chloroplatinic acid/diketone complexes, platinum black, and platinum-on-support.

The catalyst (C) may be added in an amount ranging from 0.1 to 1000 parts by weight, for example, from 1 to 100 parts by weight, as platinum metal proper per 1000 parts by weight of the total amount of the compounds (A) and (B).

The polyglycerolated silicone elastomer according to the present disclosure may be mixed with at least one oil chosen from hydrocarbon oils and silicone oils to form a gel. In these gels, the polyglycerolated elastomer may be in the form of non-spherical particles.

Such elastomers are disclosed, for example, in International Patent Application Publication No. WO 2004/024798.

Examples of suitable polyglycerolated silicone elastomers include, but are not limited to, those sold under the names "KSG-710", "KSG-810", "KSG-820", "KSG-830", and "KSG-840" by Shin Etsu.

The non-spherical silicone elastomer may be present in the composition according to the present disclosure in an amount ranging from 0.01 % to 30% by weight, with respect to the total weight of the composition, for example, from 0.1 % to 20% by weight, or from 0.2% to 10% by weight.

Oils

The composition according to the present disclosure comprises at least one oil. The at least one oil may be chosen from volatile oils, nonvolatile oils, and mixtures thereof. In at least one embodiment, the composition according to the present disclosure may comprise at least one volatile oil.

As used herein, the term "volatile oil" is understood to mean any oil capable of evaporating on contact with the skin at ambient temperature and atmospheric pressure. The volatile oils of the present disclosure are volatile cosmetic oils which are liquid at ambient temperature and which have a non-zero vapor pressure, at ambient temperature and atmospheric pressure, ranging, for example, from 0.13 Pa to 40 000 Pa (0.001 to 300 mmHg), or from 1.3 to 1300 Pa (0.01 to 10 mmHg).

The volatile oil may be chosen from volatile hydrocarbon oils, volatile silicone oils, volatile fluorinated oils, and mixtures thereof.

As used herein, the term "hydrocarbon oil" is understood to mean an oil comprising mainly hydrogen and carbon atoms and optionally at least one atom chosen from oxygen, nitrogen, sulphur, and/or phosphorus atoms.

The volatile hydrocarbon oils may be chosen from hydrocarbon oils comprising from 8 to 16 carbon atoms, for example, branched $C_8$-$C_{16}$ alkanes, such as $C_8$-$C_{16}$ isoalkanes of petroleum origin (also referred to as isoparaffins), for instance, isododecane (also known as 2,2,4,4,6-pentamethylheptane), isodecane, isohexadecane, and the oils sold under the trade names Isopars® and Permethyls®.

Other examples of suitable volatile oils include volatile silicones, for example, volatile linear or cyclic silicone oils, such as those having a viscosity $\leq$5 centistokes ($5\times10^{-6}$ m$^2$/s) and those comprising from 2 to 10 silicon atoms, for instance, from 2 to 7 silicon atoms, these silicones optionally comprising at least one group chosen from alkyl and alkoxy groups comprising from 1 to 10 carbon atoms. Non-limiting examples of volatile silicone oils suitable for use in accordance with the present disclosure include octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane, and mixtures thereof.

In at least one embodiment, the volatile fluorinated oil may not have a flash point.

Suitable volatile fluorinated oils include, for example, nonafluoroethoxybutane, nonafluoromethoxybutane, decafluoropentane, tetradecafluorohexane, dodecafluoropentane, and mixtures thereof.

The composition according to the present disclosure may comprise at least one non-volatile oil.

As used herein, the term "non-volatile oil" is understood to mean an oil which remains on the skin at ambient temperature and atmospheric pressure for at least several hours and which has, for example, a vapor pressure of less than 0.13 Pa (0.01 mmHg).

These non-volatile oils may be hydrocarbon oils, for example, hydrocarbon oils of animal and vegetable origin, silicone oils, and mixtures thereof. As used herein, the term "hydrocarbon oil" is understood to mean an oil comprising mainly hydrogen and carbon atoms and optionally at least one atom chosen from oxygen, nitrogen, sulphur, and/or phosphorus atoms.

The non-volatile oils may be chosen from non-volatile hydrocarbon oils, which, if appropriate, may be fluorinated, and/or non-volatile silicone oils.

Non-limiting examples of suitable non-volatile hydrocarbon oils include:

hydrocarbon oils of animal origin, hydrocarbon oils of vegetable origin, such as triglycerides comprising esters of fatty acids and of glycerol, the fatty acids of which may have various chain lengths ranging from $C_4$ to $C_{24}$, it being possible for these chains to be linear or branched and saturated or unsaturated; these oils may be chosen from triglycerides of heptanoic acid; triglycerides of octanoic acid; wheat germ, sunflower, grape seed, sesame, maize, apricot, castor, shea, avocado, olive, soybean, sweet almond, palm, rapeseed, cottonseed, hazelnut, macadamia, jojoba, alfalfa, poppy, pumpkinseed, sesame, cucumber, blackcurrant seed, evening primrose, millet, barley, quinoa, rye, safflower, candlenut, passionflower, and musk rose oils; shea butter; and triglycerides of caprylic/capric acids, such as those sold by Stéarineries Dubois and those sold under the names Miglyol 810®, 812®, and 818® by Dynamit Nobel;

synthetic ethers comprising from 10 to 40 carbon atoms;

linear or branched hydrocarbons of mineral or synthetic origin, such as liquid petrolatum, polydecenes, hydrogenated polyisobutene, for instance, Parleam®, squalane, liquid paraffins, and mixtures thereof;

synthetic esters, such as oils of formula $R_1COOR_2$, in which $R_1$ is chosen from residues of linear or branched fatty acids comprising from 1 to 40 carbon atoms and $R_2$ is a hydrocarbon chain, for instance, a branched hydrocarbon chain, comprising from 1 to 40 carbon atoms, with the proviso that $R_1+R_2$ is $\geq$10, for example, Purcellin oil (cetearyl octanoate); isopropyl myristate; isopropyl palmitate; $C_{12}$ to $C_{15}$ alkyl benzoates; hexyl laurate; diisopropyl adipate; isononyl isononanoate; isodecyl neopentanoate; 2-ethylhexyl palmitate; isostearyl isostearate; 2-hexyldecyl laurate; 2-octyldecyl palmitate; 2-octyldodecyl myristate; heptanoates, octanoates, decanoates, and ricinoleates of alcohols or of polyalcohols, such as propylene glycol dioctanoate; hydroxylated esters, such as isostearyl lactate, diisostearyl malate, and 2-octyldodecyl lactate; esters of polyols; and esters of pentaerythritol;

fatty alcohols which are liquid at ambient temperature with a branched and/or unsaturated carbon chain comprising from 12 to 26 carbon atoms, such as octyldodecanol, isostearyl alcohol, oleyl alcohol, 2-hexyldecanol, 2-butyloctanol, and 2-undecylpentadecanol; and higher fatty acids, such as oleic acid, linoleic acid, and mixtures thereof.

The non-volatile silicone oils which can be used in accordance with the present disclosure may be non-volatile polydimethylsiloxanes (PDMSs); polydimethylsiloxanes comprising at least one group chosen from pendent alkyl groups, pendent alkoxy groups, alkyl groups at the end of the silicone chain, and alkoxy groups at the end of the silicone chain, which groups each comprise from 2 to 24 carbon atoms; and phenylated silicones, such as phenyl trimethicones, phenyl dimethicones, phenyl(trimethylsiloxy)diphenylsiloxanes, diphenyl dimethicones; diphenyl(methyldiphenyl)trisiloxanes, and mixtures thereof.

The at least one oil may be present in the composition in an amount ranging from 1% to 80% by weight, with respect to the total weight of the composition, for example, from 5% to 60% by weight, or from 5% to 40% by weight.

Concave Silicone Particles

The composition of the present disclosure also comprises concave silicone particles, such as particles of portions of hollow spheres comprising a silicone material. The concave silicone particles may be dispersed in the fatty phase of the composition.

The concave silicone particles may have a mean diameter of less than or equal to 10 μm, for example, ranging from 0.1 μm to 8 μm, from 0.2 to 7 μm, from 0.5 to 6 μm, or from 0.5 to 4 μm.

As used herein, the term "mean diameter" is understood to mean the greatest dimension of the particle.

Portions of hollow spheres useful in accordance with the present disclosure may have the shape of truncated hollow spheres exhibiting a single orifice communicating with their central cavity and having a transverse cross section with the shape of a horseshoe or an arch.

The organosilicone material may be a crosslinked polysiloxane with a three-dimensional structure; comprising, for example, units of formula (I): $SiO_2$, and/or units of formula (II): $R^1SiO_{1.5}$, in which $R^1$ is an organic group comprising a carbon atom directly connected to the silicon atom. The organic group may be chosen from reactive organic groups and unreactive organic groups, and in at least one embodiment, may be an unreactive organic group.

The unreactive organic group may be chosen, for example, from $C_1$-$C_4$ alkyl groups, such as methyl, ethyl, propyl, and butyl groups, and phenyl groups, and may, in at least one embodiment, be a methyl group.

Examples of suitable reactive organic groups include epoxy groups, (meth)acryloyloxy groups, alkenyl groups, mercaptoalkyl groups, aminoalkyl groups, haloalkyl groups, glyceroxy groups, ureido groups, and cyano groups. In one embodiment, the reactive organic group may be chosen from epoxy groups, (meth)acryloyloxy groups, alkenyl groups, mercaptoalkyl groups, and aminoalkyl groups. The reactive organic group may comprise from 2 to 6 carbon atoms, for example, from 2 to 4 carbon atoms.

Non-limiting examples of suitable epoxy groups include 2-glycidoxyethyl groups, 3-glycidoxypropyl groups, and 2-(3,4-epoxycyclohexyl)propyl groups.

Suitable (meth)acryloyloxy groups may include, for example, 3-methacryloyloxypropyl groups and 3-acryloyloxypropyl groups.

Examples of alkenyl groups include, but are not limited to, vinyl, allyl, and isopropenyl groups.

Non-limiting examples of mercaptoalkyl groups include mercaptopropyl and mercaptoethyl groups.

Suitable aminoalkyl groups include, for example, 3-[(2-aminoethyl)amino]propyl groups, 3-aminopropyl groups, and N,N-dimethylaminopropyl groups.

Examples of haloalkyl groups include, but are not limited to, 3-chloropropyl groups and trifluoropropyl groups.

Non-limiting examples of glyceroxy groups include 3-glyceroxypropyl groups and 2-glyceroxyethyl groups.

Suitable ureido groups, include, for example, 2-ureidoethyl groups.

Examples of cyano groups include, but are not limited to, cyanopropyl and cyanoethyl groups.

In at least one embodiment, in the unit of formula (II), $R^1$ may be a methyl group.

In another embodiment, the organosilicone material may comprise units of formulas (I) and (II), in a unit (I)/unit (II) molar ratio ranging from 30/70 to 50/50, for example, from 35/65 to 45/55.

The organosilicone particles may be obtained according to a process comprising:
(a) introducing into an aqueous medium, in the presence of at least one hydrolysis catalyst and optionally at least one surfactant, a compound (III) of formula $SiX_4$ and a compound (IV) of formula $RSiY_3$, wherein X and Y, which may be identical or different, are chosen from $C_1$-$C_4$ alkoxy groups, alkoxyethoxy groups comprising a $C_1$-$C_4$ alkoxy group, $C_2$-$C_4$ acyloxy groups, N,N-dialkylamino groups comprising a $C_1$-$C_4$ alkyl group, hydroxyl groups, halogen atoms, and hydrogen, and R is an organic group comprising a carbon atom connected directly to the silicon atom; and
(b) bringing the mixture resulting from stage (a) into contact with an aqueous solution comprising at least one polymerization catalyst and optionally at least one surfactant, at a temperature ranging from 30 and 85° C., for at least two hours.

Stage (a) corresponds to a hydrolysis reaction and stage (b) corresponds to a condensation reaction.

In stage (a), the molar ratio of compound (III) to compound (IV) may range from 30/70 to 50/50, for example, from 35/65 to 45/45, or may be equal to 40/60. The ratio by weight of the water to the total weight of compounds (III) and (IV) may range from 10/90 to 70/30. The order of introduction of the compounds (III) and (IV) generally depends on their rate of hydrolysis. The temperature of the hydrolysis reaction may range from 0 to 40° C., and in at least one embodiment, does not exceed 30° C. in order to prevent premature condensation of the compounds.

The X and Y groups of the compounds (III) and (IV) may be chosen, for example, from:
$C_1$-$C_4$ alkoxy groups, such as methoxy and ethoxy groups;
alkoxyethoxy groups comprising a $C_1$-$C_4$ alkoxy group, for instance, methoxyethoxy and butoxyethoxy groups;
$C_2$-$C_4$ acyloxy groups, such as acetoxy and propionyloxy groups;
N,N-dialkylamino groups comprising a $C_1$-$C_4$ alkyl group, for instance, dimethylamino and diethylamino groups; and
halogen atoms, such as chlorine and bromine.

Examples of compounds of formula (III), include, but are not limited to, tetramethoxysilane, tetraethoxysilane, tetrabutoxysilane, trimethoxyethoxysilane, tributoxyethoxysilane, tetraacetoxysilane, tetrapropioxysilane, tetra(dimethylamino)silane, tetra(diethylamino)silane, silanetetraol, chlorosilanetriol, dichlorodisilanol, tetrachlorosilane, and chlorotrihydrosilane. In at least one embodiment, the compound of formula (III) may be chosen from tetramethoxysilane, tetraethoxysilane, tetrabutoxysilane, and mixtures thereof.

The compound of formula (III) results, after the polymerization reaction, in the formation of the units of formula (I).

The compound of formula (IV) results, after the polymerization reaction, in the formation of the units of formula (II).

The R group in the compound of formula (IV) may be chosen from the groups as described above in relation to the $R^1$ group of the compound of formula (II).

Non-limiting examples of compounds of formula (IV) comprising an unreactive organic group R include methyltrimethoxysilane, ethyltriethoxysilane, propyltributoxysilane, butyltributoxysilane, phenyltrimethoxyethoxysilane, methyltributoxyethoxysilane, methyltriacetoxysilane, methyltripropioxysilane, methyltri(dimethylamino)silane, methyltri (diethylamino)silane, methylsilanetriol, methylchlorodisilanol, methyltrichlorosilane, and methyltrihydrosilane.

Examples of compounds of formula (IV) comprising a reactive organic group R include, but are not limited to:
silanes comprising an epoxy group, such as (3-glycidoxypropyl)trimethoxysilane, (3-glycidoxypropyl)triethoxysilane, [2-(3,4-epoxycyclohexyl)ethyl]trimethoxysilane, (3-glycidoxypropyl)methyldimethoxysilane, (2-glycidoxyethyl)methyldimethoxysilane, (3-glycidoxypropyl) dimethylmethoxysilane, and (2-glycidoxyethyl)dimethylmethoxysilane;
silanes comprising a (meth)acryloyloxy group, such as (3-methacryloyloxypropyl)trimethoxysilane and (3-acryloyloxypropyl)trimethoxysilane;
silanes comprising an alkenyl group, such as vinyltrimethoxysilane, allyltrimethoxysilane, and isopropenyltrimethoxysilane;

silanes comprising a mercapto group, such as mercaptopropyltrimethoxysilane and mercaptoethyltrimethoxysilane;

silanes comprising an aminoalkyl group, such as (3-aminopropyl)trimethoxysilane, (3-[(2-aminoethyl)amino]propyl)trimethoxysilane, (N,N-dimethylaminopropyl)trimethoxysilane, and (N, N-dimethylaminoethyl)trimethoxysilane;

silanes comprising a haloalkyl group, such as (3-chloropropyl)trimethoxysilane and trifluoropropyltrimethoxysilane;

silanes comprising a glyceroxy group, such as (3-glyceroxypropyl)trimethoxysilane and di(3-glyceroxypropyl)dimethoxysilane;

silanes comprising a ureido group, such as (3-ureidopropyl)trimethoxysilane, (3-ureidopropyl)methyldimethoxysilane, and (3-ureidopropyl)dimethylmethoxysilane; and silanes comprising a cyano group, such as cyanopropyltrimethoxysilane, cyanopropylmethyldimethoxysilane, and cyanopropyldimethylmethoxysilane.

In at least one embodiment, the compound of formula (IV) comprising a reactive organic group R may be chosen from silanes comprising an epoxy group, silanes comprising a (meth)acryloyloxy group, silanes comprising an alkenyl group, silanes comprising a mercapto group, and silanes comprising an aminoalkyl group.

In another embodiment, compounds (III) and (IV) may be chosen from tetraethoxysilane and methyltrimethoxysilane.

Examples of suitable hydrolysis and polymerization catalysts include, but are not limited to, basic catalysts, such as sodium hydroxide, potassium hydroxide, sodium carbonate, sodium hydrogencarbonate, and amines (such as ammonia, trimethylamine, triethylamine, and tetramethylammonium hydroxide); and acidic catalysts chosen from organic acids, such as citric acid, acetic acid, methanesulphonic acid, p-toluenesulphonic acid, dodecylbenzenesulphonic acid, and dodecylsulphonic acid, and inorganic acids, such as hydrochloric acid, sulphuric acid, and phosphoric acid.

The optional surfactant may be chosen from nonionic surfactants, anionic surfactants, and mixtures thereof. Sodium dodecylbenzenesulphonate, for example, may be used as an anionic surfactant. The end of the hydrolysis reaction is marked by the disappearance of products (III) and (IV), which are insoluble in water, and the production of a homogeneous liquid layer.

The condensation stage (b) may use the same catalyst as the hydrolysis stage or another catalyst chosen from those mentioned above.

Upon conclusion of this process, a suspension in water of fine organosilicone particles is obtained, which particles may optionally be separated subsequently from their medium. The process described above may thus comprise an additional stage of filtration, for example, on a membrane filter, of the product resulting from stage (b), optionally followed by a stage of centrifuging the filtrate, intended to separate the particles from the liquid medium, and then by a stage of drying the particles. Other separation methods can, of course, be employed.

The shape of the portions of hollow spheres obtained according to the above process and their dimensions will depend on the method used to bring the products into contact in stage (b).

A somewhat basic pH and introduction under cold conditions of the polymerization catalyst into the mixture resulting from stage (a) may result in portions of hollow spheres with the shape of round-bottomed "bowls", whereas a somewhat acidic pH and dropwise introduction of the mixture resulting from stage (a) into a hot polymerization catalyst may result in portions of hollow spheres having a transverse cross section with the shape of a "horseshoe".

According to one embodiment of the present disclosure, portions of hollow spheres with the shape of "bowls" may be used. These particles may be obtained as disclosed, for example, in Japanese Patent Application No. 2003-128788.

Portions of hollow spheres with the shape of a horseshoe are also disclosed, for example, in Japanese Patent Application No. 2000-191789.

BRIEF DESCRIPTION OF THE DRAWING

A concave particle formed of portions of spheres with the shape of a bowl is illustrated in transverse cross section in FIG. 1. The width (W2) corresponds to the diameter of the particles.

Figure 1:
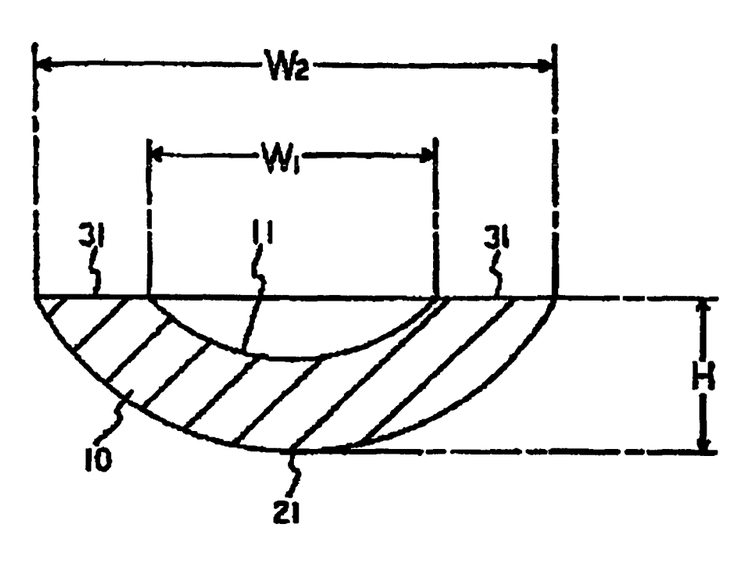

Referring to FIG. 1, the concave portions are formed (in cross section perpendicular to the plane of the opening delimited by the portion of hollow sphere) of a small internal arc (11), of a large external arc (21), and of segments (31), which connect the ends of the respective arcs, wherein the width (W1) between the two ends of the small internal arc (11) may range from 0.01 to 8 µm, for example, from 0.02 to 6 µm, on average, the width (W2) between the two ends of the large external arc (21) may range from 0.05 to 10 µm, for example, from 0.06 to 8 µm, on average, and the height (H) of the large external arc (21) may range from 0.015 to 8 µm, for example, from 0.03 to 6 µm, on average.

The average dimensions mentioned above may be obtained by calculating the mean of the dimensions of one hundred particles chosen on an image obtained with a scanning electron microscope.

Non-limiting examples of concave particles of portions of spheres which can be used according to the present disclosure include:

particles composed of the crosslinked organosilicone TAK-110 (crosslinked methylsilanol/silicate polymer) from Takemoto Oil & Fat, with the shape of a bowl, with a width of 2.5 µm, a height of 1.2 µm, and a thickness of 150 nm (particles sold under the name NLK-506 by Takemoto Oil & Fat);

particles composed of the crosslinked organosilicone TAK-110 (crosslinked methylsilanol/silicate polymer) from Takemoto Oil & Fat, with the shape of a bowl, with a width of 0.8 µm, a height of 0.4 µm, and a thickness of 130 nm (particles sold under the name NLK-515 by Takemoto Oil & Fat); and particles composed of the crosslinked organosilicone TAK-110 (crosslinked methylsilanol/silicate polymer) from Takemoto Oil & Fat, with the shape of a bowl, with a width of 7 µm, a height of 3.5 µm, and a thickness of 200 nm (particles sold under the name NLK-510 by Takemoto Oil & Fat).

These particles have the CTFA name: methylsilanol/silicate crosspolymer.

In at least one embodiment, the concave silicone particles may have a mean diameter of less than or equal to 5 µm, for example, ranging from 0.1 µm to 5 µm, from 0.2 to 5 µm, from 0.5 to 4 µm, or from 0.5 to 3 µm.

These particles with a mean diameter of less than or equal to 5 µm may make it possible to obtain greater thickening of the fatty phase than that obtained with particles with a mean diameter of greater than 5 µm. These particles may also make it possible to optimize the properties of slip, of spreading, and of comfort of the composition according to the present disclosure.

The concave silicone particles may be present in the composition according to the present disclosure in an amount ranging from 0.01 % to 50% by weight, with respect to the total weight of the composition, for example, from 0.1% to 30% by weight, or from 1% to 15% by weight.

According to one embodiment, the ratio by weight of the content of concave silicone particles to the content of silicone elastomer may range from 0.1 to 100, for example, from 0.2 to 50, or from 0.5 to 10.

According to another embodiment, the cosmetic composition of the present disclosure may comprise:
i) concave silicone particles having a mean diameter of less than 5 µm;
ii) particles of at least one non-spherical silicone elastomer; and
iii) at least one oil;
wherein the ratio by weight of the concave silicone particles to the particles of non-spherical silicone elastomer ranges from 0.1 to 100, for example, from 0.2 to 50, or from 0.5 to 10.

Additional Fatty Substances

Apart from the oils, the fatty phase of the composition according to the present disclosure may further comprise at least one additional fatty substance chosen from waxes, pasty fatty substances, and mixtures thereof.

As used herein, the term "wax" is understood to mean a fatty substance which is solid at ambient temperature (25° C.), which exhibits a reversible solid/liquid change in state, which has a melting point of greater than 30° C. which can range up to 200° C., which has a hardness of greater than 0.5 MPa, and which exhibits an anisotropic crystalline arrangement in the solid state. It may be a hydrocarbon, fluorinated, and/or silicone wax, and may be of animal, vegetable, mineral, or synthetic origin.

The wax may be chosen, for example, from beeswax; carnauba wax; candelilla wax; paraffin waxes; hydrogenated castor oil; synthetic waxes, such as polyethylene waxes (for example, those with a molecular weight ranging from 400 to 600) and Fischer-Tropsch waxes; silicone waxes, such as alkyl and alkoxy dimethicones comprising from 16 to 45 carbon atoms; ceresins and ozokerites, for example, isoparaffins having a melting point of less than 40° C., such as EMW-0003, sold by Nippon Seirou; α-olefin oligomers, such as the polymers Performa V® 825, 103, and 260 sold by New Phase Technologies; ethylene-propylene copolymers, such as Performalene® EP 700; microcrystalline waxes having a melting point of greater than 85° C., such as HI-MIC® 1070, 1080, 1090, and 3080, sold by Nippon Seirou, and mixtures thereof.

The at least one wax may be present in the composition in an amount ranging from 0.01 % to 20% by weight, for example, from 1 to 15% by weight, or from 3 to 10% by weight, with respect to the total weight of the composition.

As used herein, the term "pasty fatty substance" is understood to mean a fatty compound which exhibits a reversible solid/liquid change in state and which comprises, at a temperature of 23° C., a liquid fraction and a solid fraction. The term "pasty" is also understood to mean poly(vinyl laurate).

The pasty compound may exhibit a hardness at 20° C. ranging from 0.001 to 0.5 MPa, for example, from 0.002 to 0.4 MPa.

Pasty fatty substances suitable for use in the fatty phase of the composition according to the present disclosure include, for example, lanolins and lanolin derivatives, such as acetylated lanolins, oxypropylenated lanolins, and isopropyl lanolate, and mixtures thereof. Other examples of suitable pasty fatty substances include, but are not limited to, esters of fatty acids and esters of fatty alcohols, for instance, those comprising from 20 to 65 carbon atoms, such as triisostearyl citrate and cetyl citrate; arachidyl propionate; poly(vinyl laurate); and cholesterol esters, such as triglycerides of vegetable origin, for instance, hydrogenated vegetable oils, viscous polyesters, and mixtures thereof. Non-limiting examples of triglycerides of vegetable origin include derivatives of hydrogenated castor oil, such as "Thixinr®" from Rheox.

Additional examples of suitable pasty fatty substances include polyesters resulting from the esterification of a carboxylic acid and of an aliphatic hydroxycarboxylic acid ester, for example, Risocast® DA-L (ester resulting from the esterification reaction of hydrogenated castor oil with dilinoleic acid in proportions of 2 to 1) and Risocast® DA-H (ester resulting from the esterification of hydrogenated castor oil with isostearic acid in proportions of 4 to 3), sold by the Japanese company Kokyu Alcohol Kogyo.

Further examples of suitable pasty fatty substances include fat-soluble polyethers resulting from the polyetherification between one or more $C_2$-$C_{100}$ diols, such as $C_2$-$C_{50}$ diols. For example, the fat-soluble polyether can be the ether of dodecane diol and of polyethylene glycol (45 EO) sold under the name Elfacos ST 9 by Akzo Nobel.

In at least one embodiment, the pasty fatty substances suitable for the formulation of the cosmetic compositions in accordance with the present disclosure may be hydrogenated cocoglycerides.

The pasty fatty substances may also be chosen from pasty silicone compounds, such as polydimethylsiloxanes (PDMSs) of high molecular weight, for example, those having at least one pendent chain chosen from alkyl and alkoxy chains comprising from 8 to 24 carbon atoms and a melting point of 20-55° C., such as stearyl dimethicones, for instance, those sold by Dow Corning under the trade names DC2503® and DC25514®, and mixtures thereof.

The at least one pasty fatty substance may be present in the composition in an amount ranging from 0.01 to 20% by weight, for example, from 3 to 15% by weight, or from 5 to 10% by weight, with respect to the total weight of the composition.

Aqueous Phase

The composition according to the present disclosure may comprise an aqueous phase.

The composition according to the present disclosure may comprise water. The water may be chosen from floral water, such as cornflower water, mineral water, such as water from Vittel, water from Lucas, and water from La Roche Posay, and/or thermal water.

The composition according to the present disclosure, and in at least one embodiment, the aqueous phase, may also comprise water-miscible organic solvents (miscible at ambient temperature −25° C.), for example, monoalcohols comprising from 2 to 6 carbon atoms, such as ethanol and isopropanol; polyols comprising, for example, from 2 to 20 carbon atoms, for example, from 2 to 10 carbon atoms, or from 2 to 6 carbon atoms, such as glycerol, propylene glycol, butylene glycol, pentylene glycol, hexylene glycol, dipropylene glycol, and diethylene glycol; and glycol ethers comprising, for example, from 3 to 16 carbon atoms, such as mono-, di-, or tripropylene glycol $C_1$-$C_4$ alkyl ethers, mono-, di-, or triethylene glycol $C_1$-$C_4$ alkyl ethers, and mixtures thereof.

The aqueous phase may additionally comprise stabilizing agents, for example, sodium chloride, magnesium dichloride, and magnesium sulphate.

The aqueous phase may also comprise any water-soluble or water-dispersible compound compatible with an aqueous phase, such as gelling agents, film-forming polymers, thickeners, surfactants, and mixtures thereof.

In at least one embodiment, the aqueous phase may be present in the composition according to the present disclosure in an amount ranging from 0.5% to 85% by weight, with respect to the total weight of the composition, for example, from 5% to 75% by weight, or from 10% to 70% by weight.

In another embodiment, water may be present in the composition according to the present disclosure in an amount ranging from 0.5% to 85% by weight, with respect to the total weight of the composition, for example, from 5% to 75% by weight, or from 10% to 70% by weight.

Coloring Materials

According to one embodiment of the present disclosure, the composition may further comprise at least one coloring material.

As used herein, the term "coloring material" is understood to mean a compound capable of producing a colored optical effect when it is formulated in a sufficient amount in an appropriate cosmetic medium.

The coloring material may be chosen from pigments, pearlescent agents, glitter, fat-soluble dyes, water-soluble dyes, and mixtures thereof.

As used herein, the term "pigments" should be understood as meaning white or colored and inorganic or organic particles which are insoluble in a liquid organic phase and which are intended to color and/or opacify the composition. The pigments may be inorganic or synthetic particles of any shape which have an optical effect and which are insoluble in the medium of the composition, whatever the temperature at which the composition is manufactured.

As used herein, the term "pearlescent agents" should be understood as meaning iridescent particles, for example, pearlescent agents produced by certain shellfish in their shells and synthesized pearlescent agents, which are insoluble in the medium of the composition.

As used herein, the term "dyes" should be understood as meaning compounds, for instance, organic compounds, which are soluble in fatty substances, such as oils, or in an aqueous phase.

The at least one coloring material may be present in the composition in an amount ranging from 0.0001% to 60% by weight, with respect to the total weight of the composition, for example, from 0.1% to 20% by weight, or from 1 to 15% by weight.

According to one embodiment of the present disclosure, the coloring material may comprise at least one pigment.

The pigments may be chosen from inorganic pigments, organic pigments, and composite pigments (i.e., pigments based on inorganic and/or organic materials).

The pigments may be chosen from monochromatic pigments, lakes, pearlescent agents, and optical effect pigments, such as reflecting pigments and goniochromatic pigments.

The inorganic pigments may be chosen from metal oxide pigments; mica covered with titanium dioxide; mica covered with bismuth oxychloride; titanium oxide-coated mica covered with iron oxide; titanium oxide-coated mica covered with ferric blue; titanium oxide-coated mica covered with chromium oxide; iron oxides; titanium dioxide; zinc oxides; cerium oxide; zirconium oxide; chromium oxide; manganese violet; prussian blue; ulramarine blue; ferric blue; bismuth oxychloride; colored pearlescent pigments, such as titanium oxide-coated mica with iron oxides, titanium oxide-coated mica with, for example, ferric blue or chromium oxide, titanium oxide-coated mica with an organic pigment of the abovementioned type, and pearlescent pigments based on bismuth oxychloride; and mixtures thereof.

The organic particles intended to be coated may be chosen, for example, from:

cochineal carmine, organic pigments formed of at least one dye chosen from azo, anthraquinone, indigoid, xanthene, pyrene, quinoline, triphenylmethane, and fluoran dyes;

organic lakes and insoluble salts of acid dyes chosen from sodium, potassium, calcium, barium, aluminium, zirconium, strontium, and titanium salts of acid dyes, such as azo, anthraquinone, indigoid, xanthene, pyrene, quinoline, triphenylmethane, and fluoran dyes; these dyes may comprise at least one group chosen from carboxylic and sulphonic acid groups; and melanin pigments.

Examples of suitable organic pigments include D&C Blue No.4, D&C Brown No. 1, D&C Green No. 5, D&C Green No. 6, D&C Orange No. 4, D&C Orange No. 5, D&C Orange No.10, D&C Orange No.11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, and FD&C Yellow No. 6

The organic lake may be supported by any compatible support, such as an inorganic support, for example, particles formed of alumina, clay, zirconia, metal oxides, such as zinc oxide and titanium oxide, talc, calcium carbonate, and/or barium sulphate. In at least one embodiment, the inorganic support may be chosen from alumina, titanium oxide, and barium sulphate.

The organic lake may also be supported by a support such as rosin and aluminium benzoate.

Suitable organic lakes include, but are not limited to, D & C Red Aluminium Lake; D & C Blue Aluminium Lake; D & C Green Aluminium Lake; D & C Orange Aluminium Lake; and D & C Yellow Aluminium Lake.

The chemical compounds corresponding to each of the organic pigments mentioned above are reported, for example, in the *International Cosmetic Ingredient Dictionary and Handbook*, 1997 Edition, pages 371 to 386 and 524 to 528, published by "The Cosmetic, Toiletry and Fragrance Association", the content of which is incorporated herein by reference.

The melanine pigments useful in accordance with the present disclosure include, for example:

melanine pigments derived from natural or synthetic sources which can be obtained: (A) by oxidation of at least one indole or indoline compound, (B) by oxidative or enzymatic polymerization of melanine precursors, (C) by extraction of the melanine from substances comprising it, or (D) by culturing microorganisms. Such melanine pigments are disclosed, for example, in European Patent Application No. 0 518 773 and International Patent Application Publication Nos. WO 93/13744 and WO 93/13745.

The at least one pigment may be present in the composition according to the present disclosure in an amount ranging from 0.01% to 25% by weight, with respect to the total weight of the composition, for example, from 1 to 12% by weight, or from 3 to 8% by weight.

The fat-soluble dyes may include, for example, Sudan red, D&C Red No. 17, D&C Green No. 6, β-carotene, soybean oil, Sudan brown, D&C Yellow No. 11, D&C Violet No. 2, D&C Orange No. 5, quinoline yellow, annatto, and bromoacids.

The water-soluble dyes may be chosen, for example, from beetroot juice, methylene blue, and caramel.

Additional Fillers

The composition according to the present disclosure may optionally comprise at least one additional filler other than the elastomers and concave particles described above.

As used herein, the term "filler" should be understood as meaning colorless or white and inorganic or synthetic particles of any shape which are insoluble in the medium of the composition, whatever the temperature at which the composition is manufactured.

The additional fillers may be inorganic or organic and of any shape, for instance, platelet, spherical, and oblong shapes, and with any crystallographic form (for example, sheet, cubic, hexagonal, orthorhombic, and the like). Examples of suitable additional fillers include, but are not limited to, talc; mica; silica; kaolin; polyamide (Nylon®) powders; poly-β-alanine powders; polyethylene powders; polyurethane powders, such as the powder formed of hexamethylene diisocyanate and trimethylol hexyllactone copolymer sold under the name Plastic Powder D-400 by Toshiki; the powders formed of tetrafluoroethylene polymers (Teflon®); lauroyllysine; starch; boron nitride; polymeric hollow microspheres, such as microspheres of poly(vinylidene chloride)/acrylonitrile, for example Expancel® (Nobel Industrie), and microspheres of acrylic acid copolymers; silicone resin powders, for example, silsesquioxane powders (for instance, silicone resin powders disclosed in European Patent No. 0 293 795 and Tospearls® from Toshiba); poly(methyl methacrylate) particles; precipitated calcium carbonate; magnesium carbonate; basic magnesium carbonate; hydroxyapatite; hollow silica microspheres; glass microcapsules; ceramic microcapsules; metal soaps derived from organic carboxylic acids comprising from 8 to 22 carbon atoms, for example, from 12 to 18 carbon atoms, such as zinc stearate, magnesium stearate, lithium stearate, zinc laurate, and magnesium myristate; barium sulphate; and mixtures thereof.

The at least one additional filler may be present in the composition in an amount ranging from 0.1% to 80% by weight, with respect to the total weight of the composition, for example, from 1% to 25% by weight, or from 3% to 15% by weight.

Additives

The composition according to the present disclosure may comprise at least one additional conventional cosmetic ingredient which may be chosen, for example, from hydrophilic or lipophilic gelling and/or thickening agents, surfactants, antioxidants, fragrances, preservatives, neutralizing agents, sunscreens, vitamins, moisturizing agents, self-tanning compounds, antiwrinkle active agents, emollients, hydrophilic or lipophilic active agents, agents for combating pollution and/or free radicals, sequestering agents, film-forming agents, dermo-decontracting active agents, soothing agents, agents which stimulate the synthesis of dermal or epidermal macromolecules and/or which prevent their decomposition, antiglycation agents, agents which combat irritation, desquamating agents, depigmenting agents, antipigmenting agents, propigmenting agents, NO-synthase inhibitors, agents which stimulate the proliferation of fibroblasts and/or keratinocytes and/or the differentiation of keratinocytes, agents which act on the microcirculation, agents which act on the energy metabolism of the cells, healing agents, and mixtures thereof.

Presentation Forms

The composition according to the present disclosure may be in various forms, for example, suspensions, dispersions, solutions, gels, emulsions, such as oil-in-water (O/W), water-in-oil (W/O), and multiple (e.g., W/O/W, polyol/O/W, and O/W/O) emulsions, creams, foams, sticks, dispersions of vesicles, for instance, of ionic and/or nonionic lipids, two-phase and multi-phase lotions, sprays, powders, and pastes. The composition may be anhydrous; for example, it can be an anhydrous paste or stick. The composition may also be a leave-in composition.

According to one embodiment, the composition according to the present disclosure may be in the form of an anhydrous composition.

According to another embodiment, the composition according to the present disclosure may be in the form of a compact powder.

It is to be understood that a person skilled in the art can choose the appropriate presentation form, as well as its method of preparation, on the basis of his general knowledge, taking into account the nature of the constituents used, for example, their solubility in the vehicle, and the application envisaged for the composition.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below. In the examples that follow, the amounts of ingredients are expressed as percentages by weight with respect to the total weight of the composition, unless otherwise indicated.

EXAMPLES

Examples 1 to 14

The influence of various fillers on the viscosity of mixtures of oil and of non-spherical silicone elastomer were studied. The compositions tested are described in the tables below.

The compositions were prepared by mixing with a Rayneri mixer for 30 minutes. The viscosity of each composition was measured at 25° C. using a Brookfield viscometer equipped with a 2, 3, or 4 spindle, depending on the samples, and at a speed of 30 revolutions per minute.

| Composition | Control | 1 | 2 | 3* | 4* | 5 | 6 | 7* | 8* | 9 |
|---|---|---|---|---|---|---|---|---|---|---|
| Silicone oil[1] | 50 | 45 | 45 | 45 | 45 | 60 | 60 | 60 | 60 | 80 |
| KSG-16[2] | 50 | 45 | 45 | 45 | 45 | 30 | 30 | 30 | 30 | |
| Covabead LH85[3] | | 10 | | | | | | | | |
| Tospearl 145B[7] | | | | | | | 10 | | | |
| Sunsphere H51[4] | | | 10 | | | | 10 | | | |
| NLK-506[5] | | | | 10 | | | | 10 | | 10 |
| NLK-510[6] | | | | | 10 | | | | | |
| NLK-51[8] | | | | | | | | | 10 | |
| DC 9506[9] | | | | | | | | | | 10 |
| Viscosity (mPa · s) | 80 | 400 | 4200 | >10 0000 | 4000 | 100 | 3800 | 13 000 | 13 500 | 550 |
| Appearance | liquid | liquid | liquid | gel | liquid | liquid | liquid | liquid | liquid | liquid |

| Composition | 10 (control) | 11 | 12 | 13* | 14* |
|---|---|---|---|---|---|
| Isododecane | 50 | 45 | 45 | 45 | 45 |
| KSG 42[10] | 50 | 45 | 45 | 45 | 45 |
| Covabead LH85 | | 10 | | | |
| Sunsphere H51 | | | 10 | | |
| NLK-506 | | | | 10 | |
| NLK-510 | | | | | 10 |
| Viscosity (mPa · s) | 65 | 260 | 1700 | >100 000 | 1600 |
| Appearance | liquid | liquid | liquid | gel | liquid |

*Compositions in accordance with the present disclosure
(1) KF-96 A-6CS (viscosity 6 cst), sold by Shin Etsu.
(2) Silicone elastomer gel - Dimethicone/Vinyl Dimethicone copolymer comprising 25% of elastomer in polydimethylsiloxane, 6 cSt - sold by Shin Etsu Silicones.
(3) Hollow poly(methyl methacrylate) microspheres sold by LCW (Sensient).
(4) Amorphous silica microspheres sold by Dohkai Chemical Industries.
(5) Concave silicone particles (diameter: 2.5 μm) sold by Takemoto Oil & Fat.
(6) Concave silicone particles (diameter: 7 μm) sold by Takemoto Oil & Fat.
(7) Polymethylsilsesquioxane resin microbeads sold by GE Toshiba Silicones.
(8) Concave silicone particles (diameter: 0.8 μm) sold by Takemoto Oil & Fat.
(9) Spherical crosslinked polydimethylsiloxane powder sold by Dow Corning (diameter of 3 μm).
(10) Silicone elastomer gel - Vinyl Dimethicone/Lauryl Dimethicone copolymer comprising 25% of elastomer in isododecane - sold by Shin Etsu Silicones.

The control compositions did not comprise fillers.

Compositions 3, 4, 7, and 8 according to the present disclosure had a greater viscosity respectively than compositions 1, 2, 5, 6, and 9, as well as the control composition.

Likewise, compositions 13 and 14 of the present disclosure had a greater viscosity respectively than compositions 11 and 12 and control composition 10.

Compositions 3, 7, 8, and 13 correspond to one embodiment of the present disclosure (wherein the concave silicone particles had a diameter of less than or equal to 5 μm) and exhibit a greater viscosity respectively than compositions 4 and 14, also according to the present disclosure.

Example 15

An anhydrous foundation was prepared which had the following composition:

| | |
|---|---|
| KSG 42[1] | 20% |
| NLK-506[2] | 10% |
| Isononyl isononanoate | 20% |
| Isododecane | 15% |
| Bentone gel | 10% |
| Plastic Powder D-400[3] | 10% |
| Talc | 5% |
| Titanium dioxide | 7% |
| Iron oxide | 3% |

[1]Silicone elastomer gel - Vinyl Dimethicone/Lauryl Dimethicone copolymer comprising 25% of elastomer in isododecane - sold by Shin Etsu Silicones.
[2]Concave silicone particles (diameter: 2.5 μm) sold by Takemoto Oil & Fat.
[3]Spherical polyurethane particles sold by Toshiki Pigment.

This foundation was easily applied to the skin, with good slip and good softness to the touch. The make-up obtained was comfortable and did not tighten the skin.

Example 16

A foundation was prepared in the form of a water/oil emulsion having the following composition:

| | |
|---|---|
| NLK-506[1] | 8% |
| KSG 210[2] | 10% |
| KSG 16[3] | 5% |
| KF-6017[4] | 2% |
| Cyclopentasiloxane | 15% |
| Phenyl trimethicone | 10% |
| Titanium dioxide | 7% |
| Iron oxide | 3% |
| Magnesium sulphate | 1% |
| Butylene glycol | 9% |
| Water | q.s. for 100% |

[1]Concave silicone particles (diameter: 2.5 μm) sold by Takemoto Oil & Fat.
[2]Silicone elastomer gel - Dimethicone PEG-10/15 copolymer comprising 25% of elastomer in polydimethylsiloxane, 6 cSt - sold by Shin Etsu Silicones.
[3]Silicone elastomer gel - Dimethicone/Vinyl Dimethicone copolymer comprising 25% of elastomer in polydimethylsiloxane, 6 cSt - sold by Shin Etsu Silicones.
[4]Silicone surfactant from Shin Etsu.

The foundation obtained exhibited good slip when applied to the skin and a soft feel. The make-up obtained was comfortable and did not tighten the skin.

Example 17

A foundation was prepared in the form of a compact powder having the following composition:

| | |
|---|---|
| NLK-506[1] | 3% |
| KSG 16[2] | 3% |
| Tospearl 145B[3] | 3% |
| Talc | 30% |
| Sericite | 37% |
| Mica | 5% |
| Titanium dioxide | 4% |
| Iron oxide | 2% |
| Amyhope LL[4] | 5% |
| 2-Ethylhexyl methoxycinnamate | 5% |
| Isononyl isononanoate | 3% |

[1]Concave silicone particles (diameter: 2.5 µm) sold by Takemoto Oil & Fat.
[2]Silicone elastomer gel - Dimethicone/Vinyl Dimethicone copolymer comprising 25% of elastomer in polydimethylsiloxane, 6 cSt - sold by Shin Etsu Silicones.
[3]Polymethylsilsesquioxane resin microbeads sold by GE Toshiba Silicones.
[4]Lauroyllysine particles sold by Ajinomoto.

The composition was prepared by mixing all the powders and by then adding the binder (oils+KSG-16+NLK-506) thereto, the mixture subsequently being milled and sieved until a homogeneous mixture was obtained. This mixture was placed in a dish and then pressed under a pressure of 2 MPa.

A compact powder was thus obtained, which easily disintegrated using a sponge, and the powder removed was non-tacky, had slip, and spread easily over the skin.

Example 18

A lipstick stick was prepared which had the following composition:

| | |
|---|---|
| Polyethylene wax (Polywax 500 from Bareco) | 10 g |
| Ozokerite | 5 g |
| Microcrystalline wax | 2 g |
| 2-Octyldodecanol | 20 g |
| Diisostearyl malate | 10 g |
| Triglyceride of capric/caprylic acids (Myritol 318 from Cognis) | 30 g |
| Pigments | 7 g |
| KSG-16[1] | 10 g |
| NLK-506[2] | 6 g |

[1]Silicone elastomer gel - Dimethicone/Vinyl Dimethicone copolymer comprising 25% of elastomer in polydimethylsiloxane, 6 cSt - sold by Shin Etsu Silicones.
[2]Concave silicone particles (diameter: 2.5 µm) sold by Takemoto Oil & Fat.

The pigments were milled in the presence of a portion of the oils. The remainder of the oils were mixed with the waxes and heated to approximately 90° C.; and after homogenization, the milled pigments were added. The NLK-506 particles and the silicone gel were added last.

The mixture was subsequently poured into molds and then, after solidifying, the sticks were removed from the molds and packaged in a case.

The stick slid well over the lips and provided, after application, a lipstick film which was glossy, comfortable, and nondrying.

Example 19

An anhydrous foundation was prepared which had the following composition:

| | |
|---|---|
| KSG 42[1] | 20% |
| NLK-515[2] | 8% |
| Isononyl isononanoate | 22% |
| Isododecane | 15% |
| Bentone gel | 10% |
| Plastic Powder D-400[3] | 10% |
| Talc | 5% |
| Titanium dioxide | 7% |
| Iron oxide | 3% |

[1]Silicone elastomer gel - Vinyl Dimethicone/Lauryl Dimethicone copolymer comprising 25% of elastomer in isododecane - sold by Shin Etsu Silicones.
[2]Concave silicone particles (diameter: 0.8 µm) sold by Takemoto Oil & Fat.
[3]Spherical polyurethane particles sold by Toshiki Pigment.

This foundation was easily applied to the skin, with good slip and good softness to the touch. The make-up obtained was comfortable and did not tighten the skin.

Example 20

An anhydrous foundation was prepared which had the following composition:

| | |
|---|---|
| KSG 42[1] | 20% |
| NLK-510[2] | 12% |
| Isononyl isononanoate | 18% |
| Isododecane | 15% |
| Bentone gel | 10% |
| Plastic Powder D-400[3] | 10% |
| Talc | 5% |
| Titanium dioxide | 7% |
| Iron oxide | 3% |

[1]Silicone elastomer gel - Vinyl Dimethicone/Lauryl Dimethicone copolymer comprising 25% of elastomer in isododecane - sold by Shin Etsu Silicones.
[2]Concave silicone particles (diameter: 7 µm) sold by Takemoto Oil & Fat.
[3]Spherical polyurethane particles sold by Toshiki Pigment.

This foundation was easily applied to the skin, with good slip and good softness to the touch. The make-up obtained was comfortable and did not tighten the skin.

What is claimed is:

1. A composition comprising concave silicone particles composed of at least one silicone material chosen from crosslinked polysiloxanes with a three-dimensional structure comprising units of formula (I): $SiO_2$ and formula (II): $R^1SiO_{1.5}$, wherein $R^1$ is an organic group comprising a carbon atom directly connected to the silicon atom; and
    a fatty phase comprising at least one oil and at least one non-spherical silicone elastomers,
    wherein the at least one non-spherical silicone elastomer is present in the composition in an amount ranging from 0.01 to 30% by weight, with respect to the total weight of the composition; and
    water,
    wherein the composition is in the form of an emulsion.
2. The composition of claim 1, wherein the concave silicone particles are dispersed in the fatty phase.
3. The composition of claim 1, wherein the concave silicone particles are in the form of portions of hollow spheres.
4. The composition of claim 1, wherein the concave silicone particles have a mean diameter of less than or equal to 5 µm.

5. The composition of claim 4, wherein the concave silicone particles have a mean diameter ranging from 0.1 μm to 5 μm.

6. The composition of claim 5, wherein the concave silicone particles have a mean diameter ranging from 0.5 μm to 3 μm.

7. The composition of claim 1, wherein the concave silicone particles are in the form of portions of hollow spheres having a transverse cross section with the shape of a horseshoe or arch.

8. The composition of claim 1, wherein the organic group is chosen from reactive organic groups and unreactive organic groups.

9. The composition of claim 8, wherein the unreactive organic group is chosen from C1-C4 alkyl groups and phenyl groups.

10. The composition of claim 9, wherein the unreactive organic group is a methyl group.

11. The composition of claim 8, wherein the reactive organic group is chosen from epoxy groups, (meth)acryloyloxy groups, alkenyl groups, mercaptoalkyl groups, aminoalkyl groups, haloalkyl groups, glyceroxy groups, ureido groups, and cyano groups.

12. The composition of claim 11, wherein the reactive organic group is chosen from epoxy groups, (meth)acryloyloxy groups, alkenyl groups, mercaptoalkyl groups, and aminoalkyl groups.

13. The composition of claim 1, wherein $R^1$ is a methyl group.

14. The composition of claim 1, wherein the at least one silicone material comprises units (I) and (II) in a unit (I)/unit (II) molar ratio ranging from 30/70 to 50/50.

15. The composition of claim 14, wherein the unit (I)/unit (II) molar ratio ranges from 35/65 to 45/55.

16. The composition of claim 1, wherein the concave silicone particles are obtained according to a process comprising:
  (a) introducing into an aqueous medium, in the presence of at least one hydrolysis catalyst and optionally at least one surfactant, a compound (III) of formula SiX4 and a compound (IV) of formula RSiY3, wherein X and Y, which may be identical or different, are chosen from C1-C4 alkoxy groups, alkoxyethoxy groups comprising a C1-C4 alkoxy group, C2-C4 acyloxy groups, N,N-dialkylamino groups comprising a C1-C4 alkyl group, hydroxyl groups, halogen atoms, and hydrogen, and R is an organic group comprising a carbon atom connected directly to the silicon atom; and
  (b) bringing the mixture resulting from stage (a) into contact with an aqueous solution comprising at least one polymerization catalyst and optionally at least one surfactant, at a temperature ranging from 30 to 85° C., for at least two hours.

17. The composition of claim 16, wherein in stage (a), the molar ratio of compound (III) to compound (IV) ranges from 30/70 to 50/50.

18. The composition of claim 17, wherein in stage (a), the molar ratio of compound (III) to compound (IV) is 40/60.

19. The composition of claim 16, wherein the ratio by weight of the water to the total weight of compounds (III) and (IV) ranges from 10/90 to 70/30 in stage (a).

20. The composition of claim 16, wherein the organic group is chosen from reactive organic groups and unreactive organic groups.

21. The composition of claim 20, wherein the unreactive organic group is chosen from C1-C4 alkyl groups and phenyl groups.

22. The composition of claim 21, wherein the unreactive organic group is a methyl group.

23. The composition of claim 20, wherein the reactive organic group is chosen from epoxy groups, (meth)acryloyloxy groups, alkenyl groups, mercaptoalkyl groups, aminoalkyl groups, haloalkyl groups, glyceroxy groups, ureido groups, and cyano groups.

24. The composition of claim 23, wherein the reactive organic group is chosen from epoxy groups, (meth)acryloyloxy groups, alkenyl groups, mercaptoalkyl groups, and aminoalkyl groups.

25. The composition of claim 16, wherein R is a methyl group.

26. The composition of claim 16, wherein the hydrolysis and polymerization catalysts, which may be identical or different, are chosen from sodium hydroxide, potassium hydroxide, sodium carbonate, sodium hydrogencarbonate, ammonia, trimethylamine, triethylamine, tetramethylammonium hydroxide, citric acid, acetic acid, methanesulphonic acid, p-toluenesulphonic acid, dodecylbenzenesulphonic acid, dodecylsulphonic acid, hydrochloric acid, sulphuric acid, and phosphoric acid.

27. The composition of claim 1, wherein the concave silicone particles comprise (in cross section) a small internal arc, a large external arc, and segments which connect the ends of the respective arcs, wherein the width between the two ends of the small internal arc range from 0.01 to 8 μm on average, the width between the two ends of the large external arc range from 0.05 to 10 μm on average, and the height (H) of the large external arc ranges from 0.015 to 8 μm on average.

28. The composition of claim 1, wherein the concave silicone particles are present in an amount ranging from 0.01% to 50% by weight, with respect to the total weight of the composition.

29. The composition of claim 28, wherein the concave silicone particles are present in the composition in an amount ranging from 1% to 15% by weight, with respect to the total weight of the composition.

30. The composition of claim 1, wherein the at least one nonspherical silicone elastomer is chosen from those obtained:
  by a crosslinking addition reaction of a diorganosiloxane comprising at least one silicon-bonded hydrogen and of a polyoxyalkylene comprising at least two groups comprising ethylenic unsaturation;
  by a crosslinking addition reaction of a diorganosiloxane comprising at least one silicon-bonded hydrogen and of polyglycerolated compounds comprising groups comprising ethylenic unsaturation, optionally in the presence of a platinum catalyst;
  by a crosslinking addition reaction of a diorganosiloxane comprising at least one silicon-bonded hydrogen and of a diorganopolysiloxane comprising siliconbonded groups comprising ethylenic unsaturation;
  by a crosslinking condensation/dehydrogenation reaction between a diorganopolysiloxane comprising hydroxyl endings and a diorganopolysiloxane comprising at least one silicon-bonded hydrogen;
  by a crosslinking condensation reaction of a diorganopolysiloxane comprising hydroxyl endings and of a hydrolysable organopolysilane;
  by thermal crosslinking of an organopolysiloxane;
  by crosslinking of an organopolysiloxane by high energy radiation.

31. The composition of claim 26, wherein the at least one nonspherical silicone elastomer is obtained by a crosslinking addition reaction of a diorganopolysiloxane comprising at least two hydrogens each bonded to a silicon and a diorganopolysiloxane comprising at least two silicon-bonded groups comprising ethylenic unsaturation, optionally in the presence of a platinum catalyst.

32. The composition of claim 30, wherein the at least one non-spherical silicone elastomer is obtained by reaction of a dimethylpolysiloxane comprising dimethylvinylsiloxy endings and a methylhydropolysiloxane comprising trimethylsiloxy endings, in the presence of a platinum catalyst.

33. The composition of claim 1, further comprising at least one volatile oil.

34. The composition of claim 1, further comprising at least one nonvolatile oil.

35. The composition of claim 1, wherein the at least one non-spherical silicone elastomer is present in the composition in an amount ranging from 0.2 to 10% by weight, with respect to the total weight of the composition.

36. The composition of claim 1, wherein the ratio by weight of the concave silicone particles to the non-spherical silicone elastomers ranges from 0.1 to 100.

37. The composition of claim 36, wherein the ratio by weight of the concave silicone particles to the non-spherical silicone elastomers ranges from 0.5 to 10.

38. The composition of claim 1, wherein the fatty phase comprises a fatty substance chosen from waxes, pasty fatty substances, and mixtures thereof.

39. The composition of claim 1, further comprising at least one coloring material.

40. The composition of claim 39, wherein the at least one coloring material is chosen from pigments, pearlescent agents, glitter, fat-soluble dyes, water-soluble dyes, and mixtures thereof.

41. The composition of claim 1, further comprising at least one cosmetic ingredient chosen from hydrophilic or lipophilic gelling and/or thickening agents, antioxidants, fragrances, preservatives, neutralizing agents, sunscreens, vitamins, moisturizing agents, self-tanning compounds, antiwrinkle active agents, emollients, hydrophilic or lipophilic active agents, agents for combating pollution or free radicals, sequestering agents, film-forming agents, dermo-decontracting active agents, soothing agents, agents which stimulate the synthesis of dermal or epidermal macromolecules and/or which prevent their decomposition, antiglycation agents, agents which combat irritation, desquamating agents, depigmenting agents, antipigmenting agents, propigmenting agents, NO-synthase inhibitors, agents which stimulate the proliferation of fibroblasts and/or keratinocytes and/or the differentiation of keratinocytes, agents which act on the microcirculation, agents which act on the energy metabolism of the cells, healing agents, and mixtures thereof.

42. A cosmetic composition comprising:
i) concave silicone particles having a mean diameter of less than 5 82 m, wherein the concave silicone particles are composed of at least one silicone material chosen from crosslinked polysiloxanes with a three-dimensional structure comprising units of formula (I): $SiO_2$ and formula (II): $R^1SiO_{1.5}$, wherein $R^1$ is an organic group comprising a carbon atom directly connected to the silicon atom;
ii) non-spherical particles of at least one silicone elastomer;
iii) at least one oil;
wherein the ratio by weight of the concave silicone particles to the non-spherical particles of silicone elastomer ranges from 0.1 to 100,
wherein the at least one non-spherical silicone elastomer is present in the composition in an amount ranging from 0.01 to 30% by weight, with respect to the total weight of the composition; and
water,
wherein the composition is in the form of an emulsion.

43. A method for making up and/or caring for keratinous substances comprising applying a cosmetic composition to the keratinous substances, wherein the cosmetic composition comprises water, concave silicone particles composed of at least one silicone material chosen from crosslinked polysiloxanes with a three-dimensional structure comprising units of formula (I): $SiO_2$ and formula (II): $R^1SiO_{1.5}$, wherein $R^1$ is an organic group comprising a carbon atom directly connected to the silicon atom, and a fatty phase comprising at least one oil and at least one nonspherical silicone elastomer, wherein the at least one non-spherical silicone elastomer is present in the composition in an amount ranging from 0.01 to 30% by weight, with respect to the total weight of the composition, wherein the composition is in the form of an emulsion.

44. A method for producing a deposited layer on the skin and/or lips which is non-drying and/or which does not exhibit tightness and/or which is comfortable comprising applying a cosmetic composition to the skin and/or lips, wherein the cosmetic composition comprises water, concave silicone particles composed of at least one silicone material chosen from crosslinked polysiloxanes with a three dimensional structure comprising units of formula (I): $SiO_2$ and formula (II): $R^1SiO_{1.5}$,
wherein R1 is an organic group comprising a carbon atom directly connected to the silicon atom, and a fatty phase comprising at least one oil and at least one non-spherical silicone elastomer,
wherein the at least one non-spherical silicone elastomer is present in the composition in an amount ranging from 0.01 to 30% by weight, with respect to the total weight of the composition, wherein the composition is in the form of an emulsion.

45. The method of claim 44, wherein the deposited layer is a make-up layer.

46. The composition of claim 1, wherein the at least one non-spherical elastomer is a non-emulsifying silicone elastomer.

47. The composition of claim 1, in the form of an oil-in water emulsion.

48. The composition of claim 1, wherein the composition comprises an aqueous phase comprising 5% to 75% by weight with respect to the total weight of the composition.

* * * * *